United States Patent [19]
Bernstein et al.

[11] Patent Number: 5,832,093
[45] Date of Patent: Nov. 3, 1998

[54] UNIVERSAL STETHOSCOPE AMPLIFIER WITH GRAPHIC EQUALIZATION AND TEACHING AND LEARNING PORTS

[76] Inventors: Leslie H. Bernstein, 1 Aviemore Dr., New Rochelle, N.Y. 10804; Neil D. Bernstein, 2255 Hearst Ave., Apt. 10, Berkeley, Calif. 94709; Leonard M. Bernstein, 1530 Tennis Court Way, Encinitas, Calif. 92024; Paul L. Bernstein, 15 Wild Berry La., Pittsford, N.Y. 14534

[21] Appl. No.: 582,701
[22] Filed: Jan. 4, 1996
[51] Int. Cl.⁶ ........................................ A61B 7/04
[52] U.S. Cl. .............................................. 381/67
[58] Field of Search .................. 381/67, 74; 128/715

[56] References Cited

U.S. PATENT DOCUMENTS

| | | | |
|---|---|---|---|
| 2,159,632 | 5/1939 | Morey | 381/74 |
| 3,247,324 | 4/1966 | Cefaly et al. | |
| 4,048,444 | 9/1977 | Giampapa | 381/67 |
| 4,071,694 | 1/1978 | Pfeiffer | 179/1 ST |
| 4,254,302 | 3/1981 | Walshe | 179/1 ST |
| 4,598,417 | 7/1986 | Deno | 381/67 |
| 4,723,555 | 2/1988 | Shue | 128/715 |
| 5,025,809 | 6/1991 | Johnson et al. | 128/715 |
| 5,027,825 | 7/1991 | Phelps, Sr. et al. | 128/715 |
| 5,301,679 | 4/1994 | Taylor | 128/773 |
| 5,347,583 | 9/1994 | Dieken et al. | 381/67 |
| 5,360,005 | 11/1994 | Wilk | 128/653.1 |

OTHER PUBLICATIONS

P.M. Thorpe; "The Deaf Doctor", Aug. 19, 1978, SA Med. Journal pp. 326–328.

Stethoscopic & Phonoaudio Devices: Historical & Future Perspectives by Michael B. Selig, Nov. 18, 1992, vol. 126,#1, Amer. Heart Jnl.

*Primary Examiner*—Forester W. Isen
*Attorney, Agent, or Firm*—John Moetteli

[57] ABSTRACT

The present invention is directed to an assembly used for modifying an ordinary acoustic stethoscope to an electronically amplified stethoscope. This assembly is mechanically married to a conventional stethoscope's tubular structure. An earpiece unit which replaces the standard earpiece on the earpiece-end of the ordinary acoustic stethoscope, is positioned so the standard air column response of any ordinary acoustic stethoscope is picked up by a microphone placed inside this special earpiece unit, thus capturing the acoustic output of the parent stethoscope and transmitting it back to a preamplifier/amplifier and frequency equalizer unit (graphic equalizer). The electronic signal is then directed to a speaker located in the special earpiece unit for monitoring by the operator, or alternatively, such signal is directed to a number of other remote units for the purpose of facilitating teaching and learning.

15 Claims, 4 Drawing Sheets

UNIVERSAL STETHOSCOPE AMPLIFIER WITH GRAPHIC EQUALIZATION AND TEACHING AND LEARNING PORTS

This application is a continuation-in-part of provisional application 60/008,106 of the same name, filed Oct. 30, 1995.

BACKGROUND OF THE INVENTION

1. Field of the Invention

The present invention relates to an apparatus and method useful in detecting, amplifying and analyzing stethoscopically detected sounds. More particularly, the present invention is a universal electronic amplification assembly adaptable to common, solely acoustic stethoscopes, enabling the conversion of the acoustic wave of the existing stethoscope into an electronic signal which is subsequently amplified, equalized, balanced, and redirected to a number of different outputs, including the user's earpieces.

2. Background

Stethoscopes have long been used by physicians to monitor auscultatory sounds, and by mechanics and technicians to diagnose problems in mechanical, pneumatic and hydraulic systems. Typically, stethoscopes, are comprised of a chestpiece, a sound transmission mechanism, and an earpiece assembly. The chestpiece of a medical stethoscope is adapted to be placed against the skin of a patient for gathering auscultatory sounds. The sound transmission mechanism (usually hollow tubing) transmits the gathered sound to a singular earpiece of a monaural stethoscope, or to the pair of earpieces of a binaural stethoscope, whereby the physician or other health professional is able to monitor the sound.

Recently, specialized stethoscopes have utilized electronics for at least some portion of their sound processing path. However, each of these specialized stethoscopes is a stand alone unit, and, as such, cannot be utilized to convert a common, solely-acoustic stethoscope into a hybrid electronic and acoustic model which is able to electronically enhance and amplify the gathered sound, a feature which would significantly improve the function of the standard acoustic stethoscope by providing clear, volume controlled and balanced audio output for users who have hearing deficiencies.

U.S. Pat. No. 5,347,583, to Dieken, describes a stethoscope having a chestpiece with an electrical transducer to convert the auscultatory sounds into an electrical input signal. This signal is reconverted to an audio signal by a speaker placed within the housing, away from the earpiece. This device may be entirely electronic or may be a combination of acoustics and electronics. However, the Dieken patent does not describe a mode in which the stethoscope may function in a purely acoustic manner. Further, this is a stand alone unit and cannot be used to convert a common solely-acoustic stethoscope into an electronic version.

U.S. Pat. No. 4,598,417, to Deno, describes an electronic stethoscope in which the acoustic signal transmitted through the chestpiece is converted into an electronic signal, run through error detection circuitry, and then converted into audio form and directed to the wearer's ears. Once again, this is a stand alone unit and cannot be used to convert a common acoustic stethoscope into a hybrid stethoscope.

U.S. Pat. No. 5,025,809, to Johnson describes a means for providing a standard air column listening device with a means for digitally recording phonocardiographic sounds. Furthermore, as with the above mentioned patents, this is a stand alone device which is not intended to enable the conversion of existing acoustic stethoscopes into hybrid stethoscopes.

U.S. Pat. No. 4,071,694, to Pfeiffer discloses a combination acoustic and electronic stethoscope. The mode of operation is effected by the means of a slide valve-electrical switch located in the chestpiece. This invention requires a specially designed stethoscope head as well as a specially-designed speaker. In addition, the Pfeiffer stethoscope, is a stand alone device which does not enable the conversion of common acoustic stethoscopes into hybrid electronic stethoscopes.

U.S. Pat. No. 4,723,555, to Shue describes a stand alone electronic stethoscope which has a chestpiece having a diaphragm on one side and a bell on the other, this arrangement being provided for gathering sounds and converting these sounds to radio waves. The Shue patent, as is the case with all known prior art, does not enable conversion of a common acoustic stethoscope into a hybrid stethoscope.

A need therefore exists for a universal stethoscope attachment which converts the common acoustic stethoscope into a hybrid electronic/acoustic stethoscope, thus enabling amplification, graphic equalization, and volume and balance control features which in turn enable a user with hearing disabilities to modify the signal so as to better hear, and consequently, better analyze the signal. In addition, a need exists for such an electronic stethoscope with multiple inputs and outputs which can be used to facilitate teaching and instruction.

SUMMARY OF THE INVENTION

The present invention is directed to a universal apparatus useful in detecting and analyzing stethoscopically detected sounds such that the needs identified above are satisfied.

In accordance with one aspect of the present invention, means is provided by which an ordinary acoustic stethoscope can be converted to an electronic stethoscope. This electronic stethoscope may be used by the user to correct for amplitude and frequency loss, and may be used to permit others to hear the signal at a distance, or to permit prerecorded signals to be played to the user, or as the case may be, a number of listeners.

The main unit includes of an amplifier and controls such as for such amplifier, a graphic equalizer (0–1000 Hz recommended) and controls, volume control, balance control for the output signal, an auxiliary output jack, an auxiliary input jack, a power switch for the unit, an input lead for a pressure sensitive control switch, and combination input/output leads for the earpiece units.

A pressure sensitive on/off switch is located on the operative face of the chestpiece (the face which comes into contact with the subject under analysis). However, for stethoscopes which have a swivel and/or interchangeable chestpiece, a simple on/off switch mounted at the pivot base or receiver portion of the chestpiece replaces this pressure sensitive switch, or, alternatively, the switch is simply removed from the main unit and either a jumper is installed or another automatic bypass is activated. The external pressure sensitive on/off switch switches the output on when pressure is applied with the chestpiece against the skin or surface of the subject under analysis. In a preferred embodiment, the microphone inputs but (not the power) are switched on when pressure is applied with the chestpiece against the patient's skin (or, in the case of use with machine fault diagnosis, against the component being tested, as the case may be). When this switch is disconnected from the main unit, electrical contact is made such that the main unit functions as if the switch were in the "on" position (i.e., conductive contact is made automatically upon removal of the external switch).

A first earpiece unit consists of a housing containing a pickup microphone (unidirectional type preferred,) and a small speaker. For these purposes, a microphone (such as type EM 12B electric condenser microphone from RDI Electronics of Valhalla, N.Y.) and an earbud speaker, common to small stereophonic headsets, may be used. In a first embodiment, the housing contains a female threaded input receptacle located adjacent to and concentric with the pickup microphone, and a male threaded boss located adjacent the speaker.

A second earpiece unit is identical to any of the above embodiments of the earpiece unit, except that no pickup microphone is required. This is because the train of sound waves arriving at the earpieces are identical; thus the pickup microphone need be incorporated in only one earpiece unit, the second requiring only an earbud speaker.

In order to convert a common acoustic stethoscope, the user simply removes each earpiece from the acoustic stethoscope and threads an electronic earpiece unit onto each threaded protruding shaft of the stethoscope, the shaft presenting itself upon removal of the earpiece. The user then threads the original earpiece onto the boss provided on the earpiece unit and begins to use the existing stethoscope in the electronic mode after connecting the lead from the earpiece unit into the main unit. The main unit is designed such that it fits at the juncture, or may be clipped below the juncture of a common or typical acoustic stethoscope.

In a second embodiment, an elastomeric receiver replaces the female threaded input receptacle and allows a press-fit of the earpiece unit directly onto the hollow metal tubes after removal of the conventional earpiece. In this alternative embodiment, the portion of the earpiece unit which fits into the external auditory canal of the user's ear is integrally molded with the housing of the earpiece unit. The conventional earpieces are no longer needed. This second embodiment thus enables ease of installation (the leads do not have to be removed while the units are attached to the hollow metal tubing) and provides further universality because the elastomer will compensate for different shaft sizes and thread pitches yet still maintain concentricity with the pickup microphone.

A third embodiment is identical to the second, except that the elastomeric receiver is sized to receive the conventional earpiece end, thus making unnecessary their removal. In addition, this further enhances the universality of the assembly due to the lesser size variance of earpieces where compared with the size variability of the tubing onto which the earpieces are normally attached.

According to still another aspect of the present invention, the earpiece units, together with the input and output leads, as described above, may be characterized as a sound-gathering device for removable attachment between the earpiece-end or earpiece-ends of an acoustic stethoscope and any electronic receiver unit such as a common radio, provided that this radio has at least one microphone input lack and at least one output jack. This further expands the universal application of the present invention in that users who already own the electronic amplification and equalization equipment, need only purchase this sound-gathering device and connect it to the microphone input and speaker or headphone output lacks of their current equipment.

BRIEF DESCRIPTION OF THE DRAWINGS

Other objects and advantages of this invention will become readily apparent as the same is better understood by reference to the following detailed description when considered in connection with the accompanying drawings wherein.

DESCRIPTION OF THE PREFERRED EMBODIMENT

Figure 1:
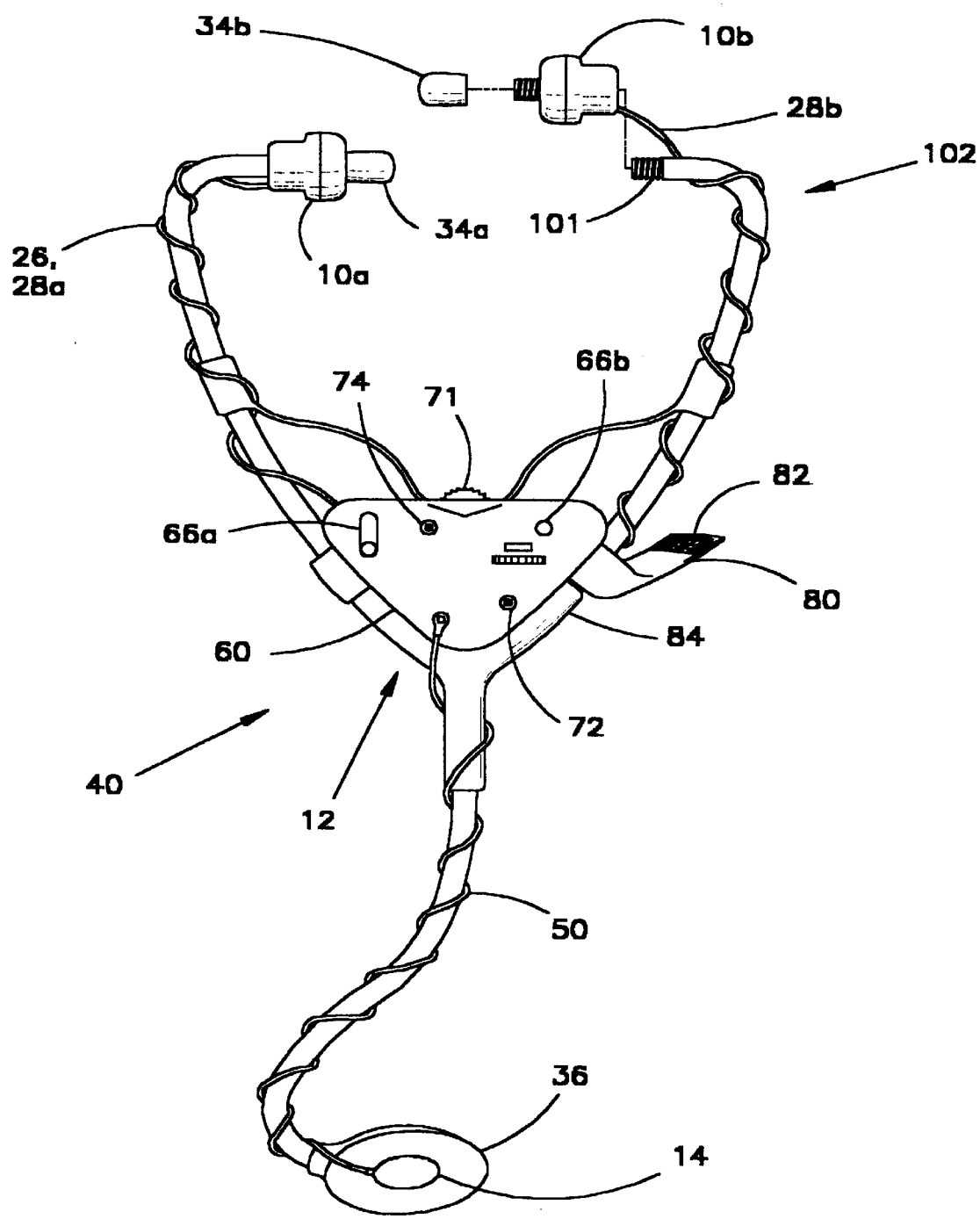
FIG. 1 shows a front elevation view of a converted acoustic stethoscope representative of the preferred embodiment.

Referring now to the drawings wherein is shown a preferred embodiment and wherein like reference numerals designate like elements throughout the several views, there is shown in FIG. 1 a front elevation view of a hybrid stethoscope representative of the preferred embodiment.

In the preferred embodiment, the universal stethoscope amplifier consists of two specialized earpiece units 10a and 10b, a main unit 12, and a pressure sensitive on/off switch 14.

Figure 3:
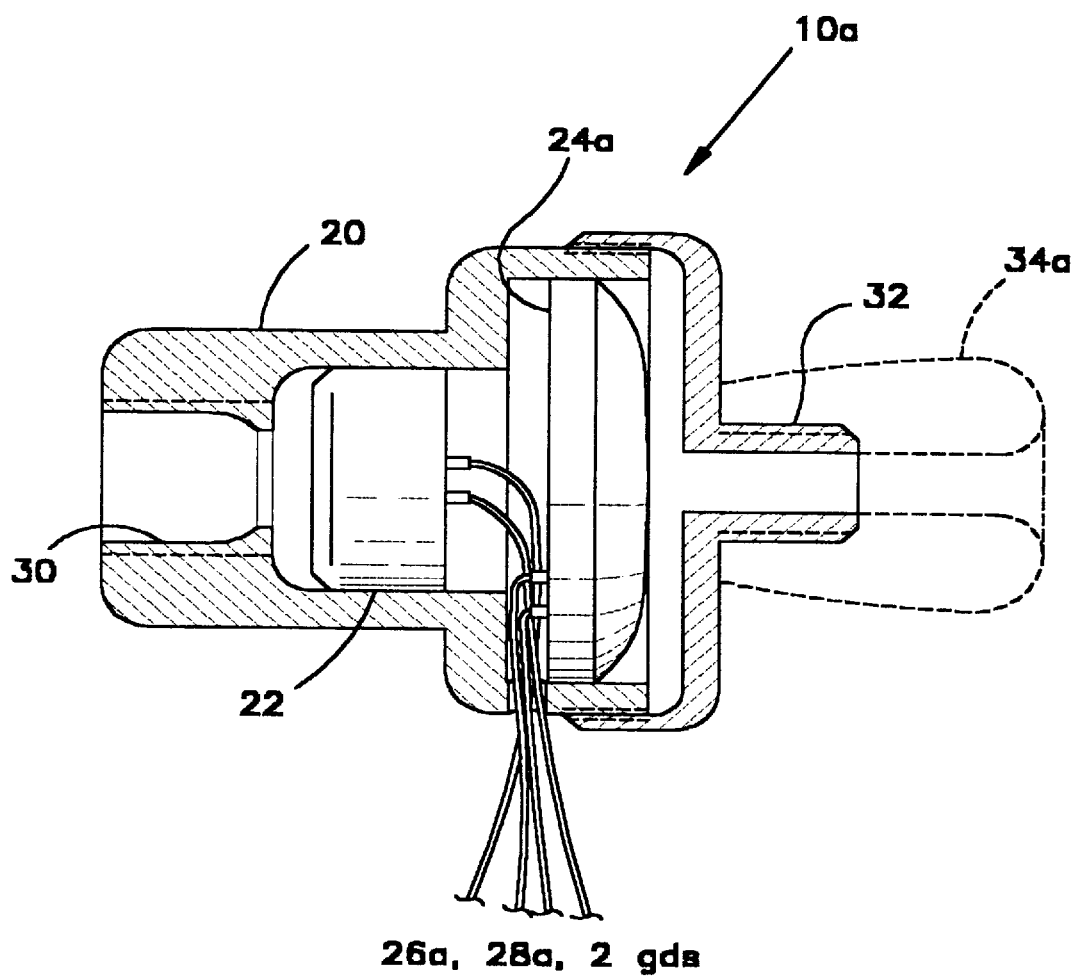
FIG. 3 shows a cross sectional view of a single earpiece unit shown in FIG. 1.

The first earpiece unit boa as seen in FIG. 3, is comprised of a housing 20, a pickup microphone 22, an output speaker 24a, an input lead 26 connected to the microphone 22, and an output lead 28a connected to speaker 24a. The input lead 26 the and output lead 28a exit the housing 20 at the bottom of the housing 20. The second earpiece unit 10b is identical but does not contain microphone 22 or the input lead 26a.

Housing 20 is formed so that a threaded receptacle 30 and a threaded boss 32 exist on opposite ends of the housing 20. The receptacle 30 is disposed directly adjacent the microphone 22, and boss 32 is situated adjacent to the speaker 24a. Receptacle 30 and the boss 32 are constructed such that the user is able to unthread the existing earpiece 34a on the acoustic stethoscope and, via the receptacle 30 or a selected adapter (not shown), is able to thread the earpiece unit boa over the threads on which the earpiece 34a or 34b had originally been threaded (on the earpiece-end 102 of the stethoscope 40). The earpiece 34a or 34b is then threaded onto the boss 32. Since the metal shaft diameter and thread pitch of stethoscopes may vary, several sizes may be provided, or alternatively (or in conjunction), adapters (not shown) may be employed where necessary, thus allowing earpiece unit 10a to work with a common, acoustic stethoscope.

Figure 4:
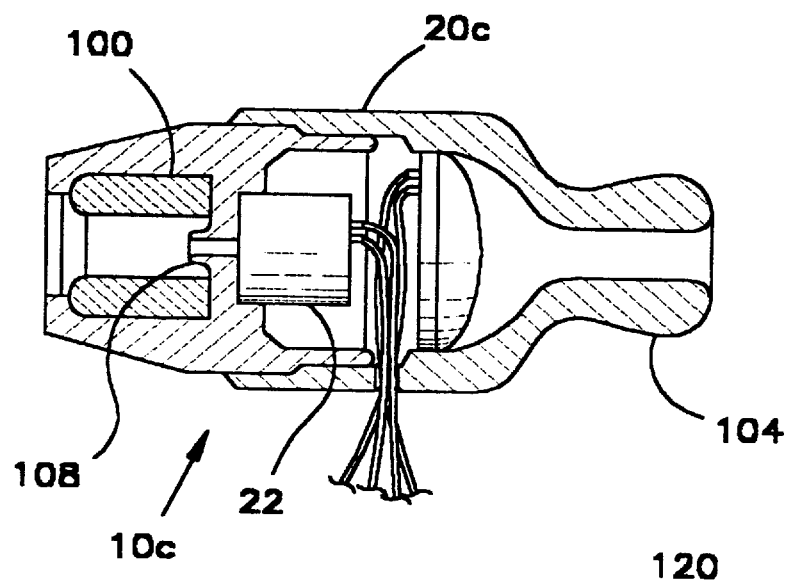
FIG. 4 shows a cross sectional view of a second embodiment of a single earpiece unit shown in FIG. 1.

In a second embodiment as shown in FIG. 4, an elastomeric receiver 100 replaces the female threaded input receptacle 30 and allows the earpiece unit 10c to be removably received, via a pre-fit, directly onto the hollow metal tube 101 on the earpiece-end 102, after having first removed conventional earpiece 34a or 34b. An annular boss 108 may also be provided to help align and stabilize the metal tube 101 on the earpiece-end 102. In this alternative embodiment, the earpiece portion 104 of the earpiece unit 10c, which fits into the external auditory canal of the user's ear is either integrally molded as part of the housing 20c of the earpiece unit 10c or otherwise attached thereto. The conventional earpieces 34a or 34b are simply no longer needed. This second embodiment thus enables ease of installation (the leads 26 or 28a or 28b do not need to be removed while the unit 10c is attached to the hollow metal tubing 101 on the earpiece-end 102) and provides further universality because the elastomer of the elastomeric receiver 100 will compensate for different shaft sizes and thread pitches yet still maintain concentricity with the microphone 22.

In still a third embodiment substantially identical to that shown in FIG. 4, the earpieces 34a and 34b need not be removed; rather, the elastomeric receiver 100 is sized to receive either conventional earpiece 34a or 34b instead of the metal tubing on the earpiece-end 102, thus increasing the universality of the universal electronic amplification assembly by taking advantage of the fact that the size and shape of a conventional earpiece 34a or 34b is more universal that the size and pitch of the metal tubing 101 and the pitch of the thread on the metal tubing on the earpiece-end 102.

A pressure sensitive on-off electric switch 14 (normally in the off position) is placed on the chestpiece 36 of the acoustic stethoscope 40. The switch 14 is tripped to the on position when a preset minimum amount of external pressure is sensed as the chestpiece 36, to which the switch 14 is attached, is pressed against a patient's body. The switch 14 is attached to the face of the chestpiece 36, which normally comes into contact with the patient's skin. In this manner, the operation of this switch 14 is automatic. The switch 14 is electrically connected to main unit 12 via lead 50, and as mentioned above, operates to enable or disable inputs from the microphone 22.

Figure 5:
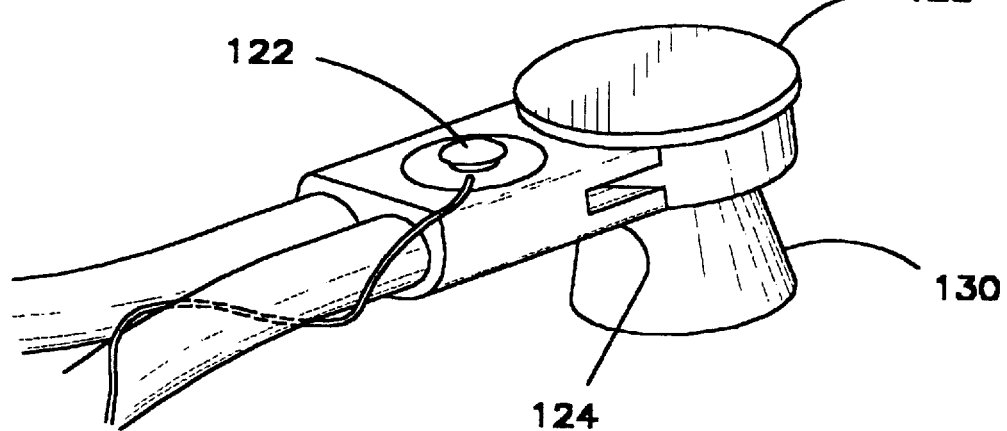
FIG. 5 shows a closeup view of the chestpiece-end of an alternate embodiment of the stethoscope assembly shown in FIG. 1.

Referring now to FIG. 5, the chestpiece-end of a stethoscope which has a swivel and/or interchangeable chestpiece-end 120, a diaphragm 128, a bell piece 130 and a swivel-point or a receiver portion 124. In this embodiment, a simple on/off switch 122 is mounted at the pivot base or receiver portion 124, thus replacing the pressure sensitive switch 14. Alternatively, the switch 14 is simply removed from the main unit 12 either and a jumper (not shown) is installed or another automatic bypass (not shown) is activated.

Figure 2:
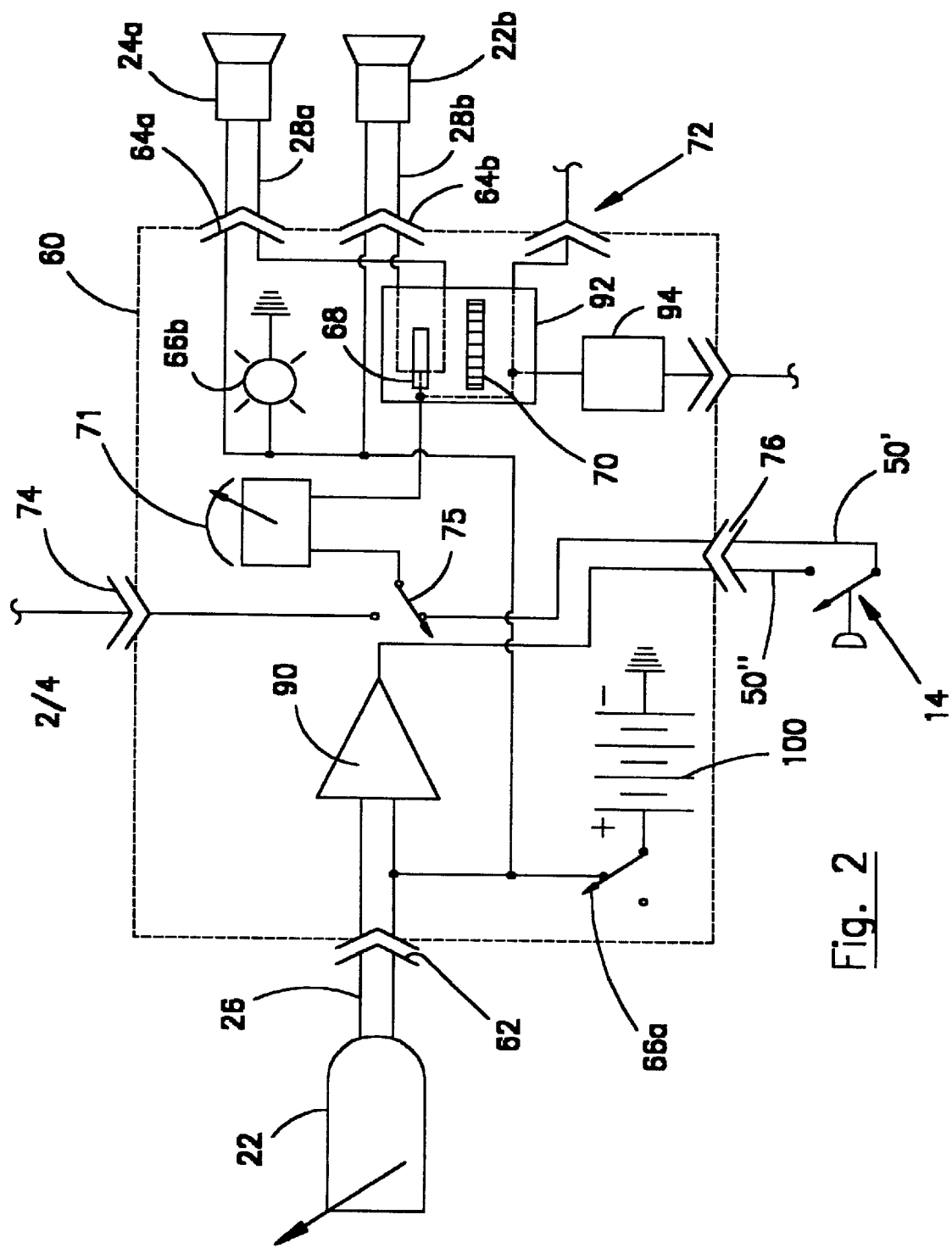
FIG. 2 shows a schematic circuit diagram of the preferred embodiment shown in FIG. 1.

The main unit 12 as shown in FIGS. 1 and 2, consists of a main unit housing 60 and various input/output ports, as well as controls and indicators provided to interface with the user/physician. The main unit housing 60 comprises a power source 100, an amplifier 90 and a graphic equalizer 92 (schematically depicted in FIG. 2). It should be emphasized that these need not be physically separate units, as such units can be interconnected on the same circuit board.

Now referring in detail to FIG. 2, in which is shown an electrical circuit diagram, an input jack 62 and output jacks 64a and 64b, located on the main unit housing 60. These jacks allow each earpiece unit boa and lob to be electrically connected to the amplifier and equalizer via input lead 26 and output leads 28a and 28b, as shown.

Also located on main unit housing 60 are a main power switch 66a, a power indicator light 66b for the electronics housed within main unit 12, a balance control 68 to regulate the output signal of main unit 12 between the left and right earpiece units 10a and 10b, and any other external output, an equalizer control 70 to allow the user to alter the frequency composition of the output signal, a volume control 71, an auxiliary output jack 72 to enable other parties to listen to the output signal or allow the external taping of the output signal, an auxiliary input jack 74, and an associated switch 75 to allow a prerecorded source to be heard, or alternatively, allow the user to listen to an output signal from output jack 72 of another unit. In addition, input jack 76 is provided to make an electrical connection with pressure sensitive switch 14 by way of leads 50' and 50".

Referring again to FIG. 1, the means which attached the main unit 12 to a common acoustic stethoscope 40 may be comprised of any number of known methods, among these are fabric tabs having mating VELCRO(™) swatches or mating snaps sewn or otherwise attached to the fabric tabs. One method, as depicted in FIG. 1, includes the use of a tab 80 attached to the outside of main unit 12, and to which VELCRO(™) may be attached both to the underside of tab 80 and to the rear panel of the main unit 12 via adhesive backing (not shown). Further, acoustic stethoscope 40 contains a fork 84, which includes the acoustic passage between the earpieces 10a and 10b and the chestpiece 36. A mating VELCRO(™) swatch, backed with adhesive, may alternatively be placed on fork 84, rather than on the rear panel of the main unit 12.

Referring again to FIG. 3, an acoustic wavefront traveling into earpiece housing 10a or 10b, via receptacle 30, impinges on microphone 22 which converts the wavefront into an electrical signal. Referring now to FIG. 2, the signal travels to an amplifier 90, and then to an equalizer 92, located in main unit 12, via input lead 26. The signal is amplified, equalized and returned to speaker 24a and 24b in earpiece unit 10a , and, as the case may be, 10b, via output lead 28a, and/or 28b. The electric output signal is then converted back into an audio signal where the user can listen through earpiece 34a or 34b, which is threaded onto boss 32. This output signal is also made available to external devices through auxiliary output jack 72. A prerecorded signal or a patch to a second device's output jack 72 can be piped into auxiliary input jack 74 of the main unit 12 from which it is rerouted to the user's ear when auxiliary input switch 75 is positioned so as to bypass inputs from the amplifier 90 and receive inputs from the external source via the jack 74. This enables the selective input of phonocardiographic sounds which are received by an instructor or which are prerecorded for the purpose of instruction, thus constituting one of several advantages of the present invention. Further, it should be noted that when the pressure sensitive switch 14 is used, the auxiliary input switch 75 is optional, due to the automatic isolation of the microphone 24 and amplifier 90 when pressure sensitive switch 14 is not depressed.

Optionally, an analog-to-digital converter 94, may be provided positioned roughly as shown in FIG. 2, and connected to the analog output of the graphic equalizer 92, thus enabling interconnection with a computer device which can display or chart the output on a screen or on some other graphical interface, thereby further enhancing the teaching utility of the present invention.

Thus, it is apparent that there has been shown and described above a universal electronic amplification assembly that can be used with the common stethoscope. However, various changes, modifications, and substitutions in the form and details of the present invention may be made by those skilled in the art without departing from the scope of the invention. Accordingly, it is appropriate that the appended claims be construed broadly and in a manner consistent with the scope of the invention.

What is claimed is:

1. A universal electronic amplification assembly for an acoustic stethoscope of the type having a chestpiece, a tubular sound transmission portion having two earpiece-ends, and an earpiece attached to each earpiece-end, the universal electronic amplification assembly comprising:

a main control unit containing one or more electric input jacks electrically connected to an amplifier, and one or more electric output jacks electrically connected from the amplifier;

two detachable electronic earpiece units, each containing an output speaker, and only one of which containing a microphone, the earpiece units having an attachment means for attaching the earpiece units to the earpiece-ends of the acoustic stethoscope;

an electrical connection between the microphone and one of the input jack or jacks; and an electrical connection between the output jack or jacks and the output speakers.

2. The assembly of claim 1, wherein the main control unit further comprises a graphic equalizer electrically connected between the amplifier and the output jacks.

3. The assembly of claim 1, wherein the main control unit further comprises one or more auxiliary output jacks electrically connected to the graphic equalizer.

4. The assembly of claim 3, wherein the microphone electrically connects to the auxiliary output jacks.

5. The assembly of claim 1, wherein the main control unit further comprises one or more auxiliary input jacks electrically connected to the amplifier.

6. The assembly of claim 3, wherein the main control unit further comprises one or more auxiliary input jacks electrically connected to the graphic equalizer.

7. The assembly of claim 1, further comprising:

one or more auxiliary input jack or jacks electrically connected from the amplifier; and a pressure sensitive switch attached to the chestpiece and electrically connected between the auxiliary input jack or jacks and the amplifier of the main control unit.

8. The assembly of claim 1 wherein, once the conventional earpiece is removed, an elastomeric receiver of the earpiece unit press-fits directly onto a hollow metal tube of the acoustic stethoscope, thus providing further universality due to the inherent ability of the elastomeric receiver to compensate for different tube shaft sizes and thread pitches.

9. The assembly of claim 1 wherein the attachment means is an elastomeric receiver which allows a press-fit of the earpiece-end of the acoustic stethoscope into the elastomeric receiver.

10. The assembly of claim 8 or 9 in which an annular boss is provided in the housing of the earpiece unit, the annular boss being concentric with the microphone and engageable with an internal surface of the portion of the tube of the earpiece-end in order that the earpiece unit may be engaged, stabilized and aligned.

11. A sound-gathering device for removable attachment between an earpiece-end of an acoustic stethoscope and an electronic receiver unit such as a common radio, such radio having at least one microphone input jack and at least one output jack, comprising:

two removable earpiece units, each comprising a housing and an output speaker, and only one of which further comprising a microphone, the earpiece unit or units being attachable to the earpiece-ends of the acoustic stethoscope;

an electrical connection between the microphone and one of the input jack or jacks; and an electrical connection between the output jack or jacks and the output speakers.

12. A universal electronic amplification assembly for an acoustic stethoscope of the type having a chestpiece, a tubular sound transmission portion, and at least one earpiece, the universal electronic amplification assembly comprising:

a main control unit containing one or more electric input jacks electrically connected to an amplifier, and one or more electric output jacks electrically connected from the amplifier;

one or more detachable electronic earpiece units, each containing an output speaker, and at least one of which containing a microphone, the earpiece units having an attachment means for attaching the earpiece units to the earpiece-ends of the acoustic stethoscope;

an electrical connection between the microphone or microphones and the input jack or jacks;

an electrical connection between the output jack or jacks and the output speaker or speakers;

one or more auxiliary input jack or jacks electrically connected from the amplifier; and a pressure sensitive switch attached to the chestpiece and electrically connected between the auxiliary input jack or jacks and the amplifier of the main control unit.

13. A universal electronic amplification assembly for an acoustic stethoscope of the type having a chestpiece, a tubular sound transmission portion, and at least one earpiece, the universal electronic amplification assembly comprising:

a main control unit containing one or more electric input jacks electrically connected to an amplifier, and one or more electric output jacks electrically connected from the amplifier;

one or more detachable electronic earpiece units, each containing an output speaker, and at least one of which containing a microphone, the earpiece units having an attachment means for attaching the earpiece units to the earpiece-ends of the acoustic stethoscope;

an electrical connection between the microphone or microphones and the input jack or jacks; and an electrical connection between the output jack or jacks and the output speaker or speakers, wherein, once the conventional earpiece is removed, an elastomeric receiver of the earpiece unit press-fits directly onto a hollow metal tube of the acoustic stethoscope, thus providing further universality due to the inherent ability of the elastomeric receiver to compensate for different tube shaft sizes and thread pitches.

14. A universal electronic amplification assembly for an acoustic stethoscope of the type having a chestpiece, a tubular sound transmission portion, and at least one earpiece, the universal electronic amplification assembly comprising:

a main control unit containing one or more electric input jacks electrically connected to an amplifier, and one or more electric output jacks electrically connected from the amplifier;

one or more detachable electronic earpiece units, each containing an output speaker, and at least one of which containing a microphone, the earpiece units having an attachment means for attaching the earpiece units to the earpiece-ends of the acoustic stethoscope;

an electrical connection between the microphone or microphones and the input jack or jacks; and an electrical connection between the output jack or jacks and the output speaker or speakers, wherein the attachment means is an elastomeric receiver which allows a press-fit of the earpiece-end of the acoustic stethoscope into the elastomeric receiver.

15. The assembly of claims 13 or 14 in which an annular boss is provided in the housing of the earpiece unit, the annular boss being concentric with the microphone and engageable with an internal surface of the portion of the tube of the earpiece-end in order that the earpiece unit may be engaged, stabilized and aligned.

* * * * *